(12) United States Patent
De Lonlay-Debeney et al.

(10) Patent No.: US 10,653,687 B2
(45) Date of Patent: May 19, 2020

(54) METHODS AND PHARMACEUTICAL COMPOSTIONS FOR TREATING RHABDOMYOLYSIS

(71) Applicants: INSERM (INSTITUT NATIONAL DE LA SANTE ET DE LA RECHERCHE MEDICALE), Paris (FR); FONDATION IMAGINE, Paris (FR); UNIVERSITE PARIS DESCARTES, Paris (FR); ASSISTANCE PUBLIQUE-HOPITAUX DE PARIS (APHP), Paris (FR); CENTRE NATIONAL DE LA RECHERCHE SCIENTIFIQUE (CNRS), Paris (FR)

(72) Inventors: Pascale De Lonlay-Debeney, Paris (FR); Corinne Lebreton, Paris (FR); Yamina Hamel, Paris (FR); Francois-Xavier Mauvais, Paris (FR); Peter Van Endert, Paris (FR)

(73) Assignees: INSERM (INSTITUT NATIONAL DE LA SANTÉ ET DE LA RECHERCHE MÉDICALE, Paris (FR); FONDATION IMAGINE, Paris (FR); UNIVERSITÉ PARIS DESCARTES ASSISTANCE PUBLIQUE-HÔPITAUX DE PARIS (APHP), Paris (FR); ASSISTANCE PUBLIQUE-HÔPITAUX DE PARIS (APHP), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/777,495

(22) PCT Filed: Nov. 16, 2016

(86) PCT No.: PCT/EP2016/077843
§ 371 (c)(1),
(2) Date: May 18, 2018

(87) PCT Pub. No.: WO2017/085115
PCT Pub. Date: May 26, 2017

(65) Prior Publication Data
US 2018/0325890 A1  Nov. 15, 2018

(30) Foreign Application Priority Data

Nov. 18, 2015 (EP) .................................. 15306831

(51) Int. Cl.
| | |
|---|---|
| A61K 48/00 | (2006.01) |
| C07H 21/02 | (2006.01) |
| C07H 21/04 | (2006.01) |
| A61K 31/4706 | (2006.01) |
| A61K 45/06 | (2006.01) |
| A61K 31/4178 | (2006.01) |
| A61K 31/365 | (2006.01) |
| A61K 31/713 | (2006.01) |
| A61P 21/00 | (2006.01) |
| A61K 31/4745 | (2006.01) |
| A61K 31/517 | (2006.01) |
| A61K 31/5377 | (2006.01) |
| A61K 31/7048 | (2006.01) |
| A61K 31/711 | (2006.01) |

(52) U.S. Cl.
CPC ........ *A61K 31/4706* (2013.01); *A61K 31/365* (2013.01); *A61K 31/4178* (2013.01); *A61K 31/4745* (2013.01); *A61K 31/517* (2013.01); *A61K 31/5377* (2013.01); *A61K 31/7048* (2013.01); *A61K 31/711* (2013.01); *A61K 31/713* (2013.01); *A61K 45/06* (2013.01); *A61P 21/00* (2018.01); *A61K 2300/00* (2013.01)

(58) Field of Classification Search
CPC .......................... A61K 31/713; C12N 15/113
See application file for complete search history.

(56) References Cited

U.S. PATENT DOCUMENTS

2011/0136845 A1  6/2011  Trawick et al.

OTHER PUBLICATIONS

J L Zimmerman: "Rhabdomyolysis", CHEST, vol. 144, No. 3, pp. 1058-1065, Sep. 1, 2013.
Michot Caroline et al: "Combination of lipid metabolism alterations and their sensitivity to inflammatory cytokines in human lipin-1-deficient myoblasts" Biochimica et Biophysica Acta. Molecular Basis of Disease, vol. 1832, No. 12, pp. 2103-2114, Aug. 6, 2013.

*Primary Examiner* — Amy H Bowman
(74) *Attorney, Agent, or Firm* — W&C IP (57) ABSTRACT

The present invention relates to methods and pharmaceutical compositions for treating rhabdomyolysis.

7 Claims, 6 Drawing Sheets

METHODS AND PHARMACEUTICAL COMPOSTIONS FOR TREATING RHABDOMYOLYSIS

FIELD OF THE INVENTION

The present invention relates to methods and pharmaceutical compositions for treating rhabdomyolysis.

BACKGROUND OF THE INVENTION

Juvenile forms of severe and recurrent rhabdomyolysis are inherited disorders characterized by the presence of myoglobinuria, serum creatinine kinase levels>10,000 IU/L and acute kidney injury [1, 2]. The precise incidence is still debated since this clinical entity is often unknown to physicians, but it is thought to represent 10-15% of the whole rhabdomyolysis in childhood. Its prognosis is poor notably because both the severity and the occurrence of further exacerbations are unpredictable [3] and the treatments remain symptomatic. Lipin-1 disease is one cause of recurrent and severe rhabdomyolysis occurring in infancy (Zeharia et al., 2008; Michot et al., 2010; Michot et al., 2012). Half of the patients die during rhabdomyolysis bouts (Bergounioux et al., 2012).

Accordingly, there is a need to develop new drugs for treating rhabdomyolysis. In this way, it has been suggested that characterization of new compounds for treatment of rhabdomyolysis may be highly desirable.

Therefore there is a crucial need to identify the pathogenic mechanisms involved in rhabdomyolysis flares, although some of them have been already characterized. Indeed, the clinical spectrum of severe and recurrent juvenile rhabdomyolysis appears quite heterogeneous regarding the nature of the different diseases. However they share a common mechanism responsible for myoglobinuria: these defects lead to an impairment in adenosine triphosphate metabolism and to a deregulation of Na+/K+ or Na+/Ca2+ ion channels and finally to a rapid increase of cytoplasmic ionized calcium concentration that leads to the destruction of the muscle cell [1, 4, 5].

Inherited rhabdomyolyses are precipitated and worsened by febrile illness or exercise, two conditions well known to be associated with high circulating levels of pro-inflammatory mediators such as cytokines and chemokines [6-8] and high temperature. Also, the inventors recently showed that rhabdomyolysis due to aldolase A deficiency involves an exacerbation of enzyme deficiency at high temperatures [9].

Potential links between metabolic diseases and chronic inflammation have already been reported in various contexts such as type 2 diabetes, obesity or atherosclerosis [6-8] leading to the proposition of immunometabolism as an emerging frontier [10]. In type 2 diabetes, various circulating inflammatory mediators have been detected such as Tumor Necrosis Factor (TNF), interleukins (IL) or adipokines. Attention has recently shifted to IL-1β which is now incriminated as one of the main pathogenic actor, by activating the c-Jun NH-(2)-terminal kinase (JNK) and triggering serine phosphorylation of insulin receptor substrate-1 (IRS1). IL-1β impairs the insulin-Phosphatidylinositol-3 kinase (PI3K)-Akt signaling pathway in insulin-sensitive tissues contributing to insulin resistance. Regarding inherited metabolic disorders, inflammation strongly contributes to the pathogenesis of Majeed syndrome [11, 12] and Mevalonate Kinase deficiency [13] that both belong to the clinical spectrum of auto-inflammatory disorders [14, 15]. Majeed syndrome is due to LPIN2 defect, a homologue of LPIN1, which controls triacylglycerol (TAG) synthesis, JNK/AP-1 (Jun N-terminal kinase and transcription factor AP-1) pathway activation and ultimately the up-regulation of pro-inflammatory genes under palmitic stimulation [14]. As direct evidence, biotherapies targeting the IL-1-related pathways have improved the outcomes of these two conditions. Of interest, some inherited metabolic disorders have reported a direct toxicity of inflammatory mediators in target organs, as this is the case for neurotoxicity of glutamate that, in type 1 glutaric aciduria, is potentiated by TNF-α [16-19].

The picture is less clear regarding skeletal muscle. Despite clear clinical evidence for its presence, no report has investigated the role of inflammation during the course of severe and recurrent juvenile rhabdomyolysis so that important questions remain to be addressed. The inventors and others reported lipin-1 (LPIN1) mutations as a cause of severe and recurrent rhabdomyolysis triggered by febrile illness or exercise [20-24]. Lipin-1 (phosphatidic acid phosphatase 1, PAP1, EC 3.1.3.4) dephosphorylates phosphatidic acid (PA) to DiAcylGlycerol (DAG), a common precursor for triglycerides (TAG) and phospholipid (PL) synthesis [25, 26]. It also has transcriptional co-regulator activity, which, through association with PPARα, PGC-1α, SREBP1 or NFATc4, regulates lipid metabolism and the mitochondrial respiratory chain [27-30]. Primary myoblasts from patients exhibit a dramatic decrease in LPIN1 expression and PAP1 activity, associated with a significant accumulation of lipid droplets (LD) [31]. This lipid myopathy has been explained in partly by an overexpression of ACACB, the gene encoding acetyl-CoA carboxylase beta, a key enzyme in the fatty acid synthesis/oxidation balance, that is associated with a decrease of Carnitine PalmitoylTransferase I (CPT1) activity in the presence of pro-inflammatory conditions (TNF-α+IL-1ß) [31]. Lpin1$^{fld/fld}$ mice also present similar muscle lipid accumulation, recently described as the consequence of a blockade in autophagic flux and accumulation of aberrant mitochondria [32].

The inventors demonstrated that the pathogenic mechanism of rhabdomyolysis in lipin-1-deficient patients combines the predisposing constitutive impairment of lipid metabolism and its exacerbation by pro-inflammatory cytokines; crucial questions on the existence of a deregulation in the inflammatory responses and their underlying mechanisms remained. Accordingly, lipins are expressed in human and other species' macrophages [14, 33-35], and lipin-1 has been suggested to be an anti-inflammatory enzyme by repressing Nuclear Factor of Activated T-Cells Cytoplasmic, Calcineurin-Dependent (NFATc)-4 [28] and Monocyte Chemoattractant Protein (MCP)-1 activities [36].

The innate immune system acts as the first line of defense against invading pathogens. Induction of antiviral innate immune responses depends on a family of innate immune receptors, the Toll-like receptors (TLR) which detect "danger signals", activate signaling pathways and induce inflammatory responses [37, 38, 39]. TLRs are present either at the cell surface or in endosomal compartments, TLR9 being an example for the latter case [40]. Importantly, a new TLR transduction mechanism impinges directly on $Ca^{2+}$ transfer [41], the final step responsive for rhabdomyolysis.

A membrane lipid network important for the regulation of TLR activation and signaling has been recently described {Koberlin, 2015 #2452} {Kano, 2011 #2143}. In the same way, the regulation of Ras-related in brain (Rab) proteins, that tightly control the innate immune system {Jahn, 1999 #2154}, is dependent of their immediate lipid microenvironment [43]. Rab proteins regulate the trafficking between the different subcellular membranous compartments of eukaryotic cells [42]. A Rab7 like protein called Rab7b, also localized on late endosomes and lysosomes, and mainly expressed in innate immune cells and muscle, has recently been involved in retrograde protein transport [43-45]. Rab7b downregulates TLR9 and TLR4 by regulating the transport from late endosomes to the trans golgi network {Yao, 2009 #2062; Wang, 2007 #2063; Ge, 2014 #2155; {Bucci, 2010 #2058; Klaver, 2015 #2372}. Recently an additional role for Rab7b has been described in skeletal muscle in the control of actin remodeling [46]. The phospholipid compositions of the different subcellular organelles differ from each other [47], notably one of the characteristic features of early endosomes is their high content of phosphatidylinositol 3-Phosphate (PI3P class III)[48, 49]. PI3P has received a lot of attention with respect to endocytosis and signal transduction via endosomes [49-53, 54{Gillooly, 2003 #2294, 55], notably in skeletal muscle [56]. Remarkably, Phosphatidic Acid Phosphatases (PAP) play a role in this lipid environment, as the knock-down of Pah1 activity, the single yeast homologue of the Lipin family, has been involved in the decrease of the PI-3-kinase Vps34p and of its product PI3P. This results in a reduction of Rab proteins including Rab Ypt7p, Vps34p and Vps39p, a subunit of the HOPS (homotypic fusion and vacuole protein sorting) tethering complex, which are required for SNARE activity and vacuole fusion [57]. Zhang et al demonstrated that lipin-1 PAP activity defect lead to autophagy blockade by decreasing the PKD-Vps34 cascade [32] in rhabdomyolysis statin-induced in LPIN1$^{fld/fld}$ mice.

The inventors investigated innate immunity in lipin-1 patients, and showed an excessive release of pro-inflammatory mediators, which was explained by a hyper-sensitivity of immune and non-immune cells to TLR-9 ligands, the latter phenomenon resulting from an alteration in the endosomal PI3P content and architecture, and a down-regulation of Rab7b responsive for a blockage of TLR9 retrograde transport. Hyperactivity of TLR9 leads to an increase of intra-cellular calcium, responsive for skeletal muscle lysis. This allowed the inventors to propose calcium flux investigation as an original method to study Lipin-1 disease and appropriate treatments, and to consider TLR9 antagonists or inhibitors and anti-calcic drugs to prevent further relapses in patients.

There is no previous disclosure in the art of the role of TLR9 in rhabdomyolysis, and the use of TLR9 antagonists and inhibitors of TLR9 expression in the treatment of rhabdomyolysis.

SUMMARY OF THE INVENTION

The present invention relates to a compound selected among TLR9 antagonists and inhibitors of TLR9 expression for use in the treatment of rhabdomyolysis in a subject in need thereof.

DETAILED DESCRIPTION OF THE INVENTION

The inventors investigated the presence of inflammatory mediators and their role in triggering rhabdomyolysis using samples from patients and controls under basal or stimulated conditions. The inventors also investigated the consequences of LPIN1 mutations by biochemical assays (enzyme activity), confocal microscopy & Imagestream technology (cellular architecture/autophagic flux/PI3K activity) and flow cytometry (signaling pathways). The inventors also tested the ability of various stimuli to alter calcium flux in patients' myoblasts, a typical feature of rhabdomyolysis.

Inflammatory molecules detected in patients' sera correlated with disease activity and related to a hypersensitivity to TLR-9 ligand. IFN-alpha activity was detected in patients with an active disease, an observation reminiscent of interferonopathies or viral infections. CpG-A and starvation, but not other TLR agonists, induced altered calcium flux in patients' myoblasts leading to cell death. Moreover, TLR-9 signaling and/or trafficking were impaired. These unexpected findings were associated with alterations in the endosomal architecture, most likely due to defective retrograde protein transport or/and decreased PI3K activity and consecutively a decrease of Rab7b expression in endosomes. Confirming the direct participation of TLR9, secretion of IL-6 after stimulation by CpG-A was abolished when myoblasts were pre-treated with a G-rich inhibitory oligonucleotide (ODN-i). The inventors have also shown that the pre-treatment with chloroquine and primaquine is sufficient to abolish IL-6 secretion and intracellular calcium mobilization in patient myoblasts stimulated with CpG-A. Moreover, chelation of intracellular calcium using dantrium sodium inhibited elevation of intracellular calcium. The inventors demonstrated that LPIN1 mutations strikingly alter homeostasis of endosomal system, leading to defects in both autophagic flux and TLR-9 trafficking. The inventors also demonstrated that patients treated with TLR9 antagonist induce a decrease of muscle pain and a dramatic decrease of pro-inflammatory cytokines (IL-8, RANTES, MCP-1) in sera.

Accordingly, the present invention relates to a compound selected from the group consisting of TLR9 antagonists and inhibitors of TLR9 expression for use in the treatment of rhabdomyolysis in a subject in need thereof.

As used herein, the term "subject" denotes a mammal. Typically, a subject according to the invention refers to any subject (preferably human) afflicted with or susceptible to be afflicted with rhabdomyolysis. In a particular embodiment, the term "subject" refers to a subject afflicted with or susceptible to be afflicted with juvenile forms of severe and recurrent rhabdomyolysis. In a particular embodiment, the term "subject" refers to a subject afflicted with or susceptible to be afflicted with Lipin-1 related juvenile forms of severe and recurrent rhabdomyolysis.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "rhabdomyolysis" has its general meaning in the art and refers to rhabdomyolysis such as revised in the World Health Organization Classification M62.8, T79.5 and T79.6. The term "rhabdomyolysis" refers to a complex medical condition involving the rapid dissolution of damaged or injured skeletal muscle. This disruption of skeletal muscle integrity leads to the direct release of intracellular muscle components, including myoglobin, Creatine kinase (CK), aldolase, and lactate dehydrogenase, as well as electrolytes, into the bloodstream and extracellular space. Rhabdomyolysis ranges from an asymptomatic illness with elevation in the CK level to a life-threatening condition associated with extreme elevations in CK, electrolyte imbalances, Acute Renal Failure (ARF), and disseminated intravascular coagulation. Although rhabdomyolysis is most often caused by direct traumatic injury, the condition can also be the result of drugs, toxins, infections, muscle ischemia, electrolyte and metabolic disorders, genetic disorders such as Lipin-1 mutations, exertion or prolonged bed rest, and temperature-induced states such as Neuroleptic Malignant Syndrome (NMS) and Malignant Hyperthermia (MH). Massive necrosis, manifested as limb weakness, myalgia, swelling, and commonly gross pigmenturia without hematuria, is the common denominator of both traumatic and nontraumatic rhabdomyolysis (Torres et al., 2015; Zimmerman and Shen, 2013; Zutt et al., 2014). The term "rhabdomyolysis" also relates to juvenile forms of severe and recurrent rhabdomyolysis, which are inherited disorders characterized by the presence of myoglobinuria, high serum creatinine kinase levels and acute kidney injury [1, 2]. The term "rhabdomyolysis" also relates to Lipin-1 related rhabdomyolysis and Lipin-1 related juvenile forms of severe and recurrent rhabdomyolysis caused by LPIN1 mutations.

As used herein, the term "TLR9" has its general meaning in the art and refers to the Toll-like receptor 9, a member of a family of innate immune receptors, the TLRs which detect "danger signals", activate signaling pathways and induce inflammatory responses [37, 38, 39]. TLRs are present either at the cell surface or in endosomal compartments, the latter being the case for TLR9 [40]. The term "TLR9" also refers to CD289 (Cluster of Differentiation 289).

The term "TLR9 antagonist" refers to a compound that selectively blocks or inactivates TLR9. As used herein, the term "selectively blocks or inactivates" refers to a compound that preferentially binds to and blocks or inactivates TLR9 with a greater affinity and potency, respectively, than its interaction with the other sub-types or isoforms of TLR family (such as TLR3, TLR7 and TLR8). Compounds that prefer TLR9, but that may also block or inactivate other TLR sub-types, as partial or full antagonists, are contemplated. The term "TLR9 antagonist" refers to any compound that can directly or indirectly block the signal transduction cascade related to the TLR9. The "TLR9 antagonist" may also consist in compounds that inhibit the binding of the TLR9 ligand CpG oligonucleotide (cytidine-phosphate-guanosine oligonucleotide) to TLR9 such as compounds having the ability to bind CpG oligonucleotide with high affinity and specificity or compounds that compete with CpG oligonucleotide. The term "TLR9 antagonist" also refers to inhibition of endosomal TLR9 activation by either inhibiting endosomal acidification, thereby preventing proteolytic maturation of endosomal TLRs, or by intercalation to nucleic acid ligands, thereby preventing their binding to TLRs. Typically, a TLR9 antagonist is a small organic molecule, an oligonucleotide, a polypeptide, an aptamer or an intra-antibody.

Tests and assays for determining whether a compound is a TLR9 antagonist are well known by the skilled person in the art such as described in Hoque et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; and CN101712957.

The TLR9 antagonists are well-known in the art as illustrated by Hoque et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; and CN101712957.

In one embodiment of the invention, the TLR9 antagonist is an oligonucleotide such as CpG ODNi (cytidine-phosphate-guanosine oligonucleotide inhibitors) such as CpG ODN 2088; CpG-ODN c41; IMO3100; IMO8400; IRS954 (DV1079); ALX-746-351; single-stranded phosphorothioate oligodeoxynucleotide antagonist such as DV056 and oligonucleotides described in Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; WO 2012/022948; WO 2009/023819; WO 2011/041311; WO 2011/159958; CN101712957.

In one embodiment of the invention, the TLR9 antagonist is a compound, such as (−)-morphinans and (+)-morphinan derivatives such as COV08-0064; COV08-0093; nucleic acid binding polymers and other nucleic acid binding agents, including antimalarials such as chloroquine, primaquine and imidazoquinolines; 4-Amino-Quinolines; Quinazolines; CMZ 203-84; CMZ 203-85; CMZ 203-88; CMZ 203-88-1; CMZ 203-89; CMZ 203-91; aminoquinolines such as hydroxychloroquine and hydroxychloroquine sulfate (plaquenil); quinacrine; bafilomycin A; CPG52364 and compounds described, for example in Hoque et al., 2013; WO 2005/007672; WO 2011/009015; WO 2012/022948; WO 2011/041311.

In another embodiment, the TLR9 antagonist of the invention is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against TLR9 of the invention as above described, the skilled man in the art can easily select those inhibiting TLR9.

In one embodiment, the compound of the invention is an inhibitor of TLR9 expression.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs, which are modified, by processes such as capping, polyadenylation, methylation, and editing, and proteins (e.g., TLR9) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit the expression of a gene.

Inhibitors of TLR9 expression for use in the present invention may be based on antisense oligonucleotide constructs. Anti-sense oligonucleotides, including anti-sense RNA molecules and anti-sense DNA molecules, would act to directly block the translation of TLR9 mRNA by binding thereto and thus preventing protein translation or increasing mRNA degradation, thus decreasing the level of TLR9 proteins, and thus activity, in a cell. For example, antisense oligonucleotides of at least about 15 bases and complementary to unique regions of the mRNA transcript sequence encoding TLR9 can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of TLR9 expression for use in the present invention. TLR9 gene expression can be reduced by contacting the subject or cell with a small double stranded RNA (dsRNA), or a vector or construct causing the production of a small double stranded RNA, such that TLR9 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of TLR9 expression for use in the present invention. Ribozymes are enzymatic RNA molecules capable of catalysing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of TLR9 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of TLR9 expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing TLR9. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; Simian Virus (SV)40-type viruses; polyomaviruses; Herpes viruses; papilloma viruses; vaccinia virus; poliovirus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent pro-viral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and Adeno-Associated Viruses (AAV), which are double-stranded DNA viruses that have already been approved for human use in gene therapy. AAV can be engineered to be replication deficient and is capable of infecting a wide range of cell types and species. It further has advantages such as, heat and lipid solvent stability; high transduction frequencies in cells of diverse lineages, including hematopoietic cells; and lack of super-infection inhibition thus allowing multiple series of transductions. Reportedly, AAV can integrate into human cellular DNA in a site-specific manner, thereby minimizing the possibility of insertional mutagenesis and variability of inserted gene expression characteristic of retroviral infection. In addition, wild-type AAV infections have been followed in tissue culture for greater than 100 passages in the absence of selective pressure, implying that AAV genomic integration is a relatively stable event. AAV can also function in an extra-chromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pUC18, pUC19, pRC/CMV, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected either by intramuscular, intradermal, subcutaneous, or other routes. It may also be administered by intranasal sprays or drops, rectal suppository and orally. It may also be administered into the epidermis or a mucosal surface using a gene-gun. Plasmids may be given in an aqueous solution, dried onto gold particles or in association with another DNA delivery system including but not limited to liposomes, dendrimers, cochleate and microencapsulation.

Typically the compounds according to the invention as described above are administered to the subject in a therapeutically effective amount.

By a "therapeutically effective amount" of the compound of the present invention as above described is meant a sufficient amount of the compound for treating rhabdomyolysis at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the compound of the present invention for the symptomatic adjustment of the dosage to the subject to be treated. A medicament typically contains from about 0.01 mg to about 500 mg of the compound of the present invention, preferably from 1 mg to about 100 mg of the compound of the present invention. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the compound according to the invention may be used in a concentration between 0.01 μM and 20 μM, particularly, the compound of the invention may be used in a concentration of 0.01, 0.05, 0.1, 0.5, 1.0, 2.5, 5.0, 10.0, 15.0, 20.0 μM.

In a further aspect, the present invention relates to the compound according to the invention in combination with one or more anti-rhabdomyolysis compounds for use in the treatment of rhabdomyolysis in a subject in need thereof.

The term "anti-rhabdomyolysis compounds" has its general meaning in the art and refers to compounds used in rhabdomyolysis therapy such as compounds used in preventing renal function and restoring metabolic derangements such as IV fluid (IVF), isotonic saline, Lactated Ringer's, diuretics, bicarbonate, mannitol, corticosteroids, acetazolamide, antioxidants, acetaminophen, and L-carnitine. The rhabdomyolysis therapy also relates to hemodialysis, alkalization of the urine and continuous renal replacement therapy (CRRT) (Zimmerman and Shen, 2013; Zutt et al., 2014). The term "anti-rhabdomyolysis compounds" also refers to anti-calcic drugs and compounds inhibiting calcium influx into the cytoplasm such as dantrium (dandrolene), bromocriptine, phenytoin, bepridil, calcium channel blockers such as dihydropyridine agents such as nifedipine (ADALATE), amlodipine (AMLOR), felodipine (FLODIL), isradipine (ICAZ), lacidipine (CALDINE), nicardipine (LOXEN), nitrendipine (BAYPRESS), and nimodipine (NIMOTOPE); and non-dihydropyridine agents such as verapamil (phenylalkylamine class) and diltiazem (benzothiazepine class).

According to the present invention, the compound of the invention is administered sequentially or concomitantly with one or more anti-rhabdomyolysis compounds.

The present invention also relates to a method for treating rhabdomyolysis in a subject in need thereof, comprising the step of administering to said subject the compound of the invention.

In a further aspect, the present invention relates to a method of screening a candidate compound for use as a drug for the treatment of rhabdomyolysis in a subject in need thereof, wherein the method comprises the steps of:
  providing a TLR9, providing a cell, tissue sample or organism expressing a TLR9,
  providing a candidate compound such as small organic molecule, an oligonucleotide, a polypeptide, an aptamer or an intra-antibody,
  measuring the TLR9 activity and calcium influx,
  selecting positively candidate compounds that inhibit TLR9 activity or inhibit calcium influx.

Methods for measuring TLR9 activity are well known in the art. For example, measuring the TLR9 activity involves determining a Ki on the TLR9 cloned and transfected in a stable manner into a CHO cell line, measuring one or more of the second messengers of the TLR9 (MyD88, IRAK, TRAF6 and TAK1), measuring TLR9 inflammatory mediators such as NF-κB, IL-6 and interferon stimulated genes such as IF27 and SIGLEC-1 and using HEK-Blue TLR9 cell line expressing a TLR9-responsive, NF-κB-inducible, SEcreted placental Alkaline Phosphatase (SEAP), measuring intracellular calcium flux in the present or absence of the candidate compound (Hogue et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; CN101712957).

Tests and assays for screening and determining whether a candidate compound is a TLR9 antagonist are well known in the art (Hogue et al, 2013; Matin et al., 2015; Jiang et al., 2013; Kader et al., 2013; David et al., 2013; Kandimalla et al., 2013; Li et al., 2011; Wang et al., 2009; Yu et al., 2009; Zhang et al., 2010; Zhu et al., 2013; U.S. Pat. No. 7,498,409; WO 2005/007672; WO 2011/009015; WO 2012/022948; WO 2009/023819; WO 2011/041311; WO 2011/159958; CN101712957). In vitro and in vivo assays may be used to assess the potency and selectivity of the candidate compounds to inhibit TLR9 activity.

Activities of the candidate compounds, their ability to bind TLR9 and their ability to inhibit TLR9 activity may be tested using isolated B cells, monocytes, Natural Killer (NK) cells, plasmacytoid Dendritic Cells (pDCs), myoblasts or HEK293 cells expressing TLR9, CHO cell line cloned and transfected in a stable manner by the human TLR9.

Activities of the candidate compounds and their ability to bind to the TLR9 may be assessed by the determination of a Ki on the TLR9 cloned and transfected in a stable manner into a CHO cell line, measuring one or more of the second messengers of the TLR9 (MyD88, IRAK, TRAF6 and TAK1), measuring TLR9 inflammatory mediators such as NF-κB, IL-6 and interferon stimulated genes such as IF27 and SIGLEC-1 and using HEK-Blue TLR9 cell line expressing a TLR9-responsive, NF-κB-inducible, secreted placental alkaline phosphatase (SEAP) in the present or absence of the candidate compound. The ability of the candidate compounds to inhibit TLR9 activity may be assessed by measuring indicators such as endogenous gene product whose expression is induced by NFκB, such as a cytokine including IL-12, IFN-γ, IL-1, TNF-α, IL-6 and other inflammatory cytokines and measuring the decrease of intracellular calcium flux.

Cells expressing another TLR than TLR9 may be used to assess selectivity of the candidate compounds.

Methods for measuring calcium influx are well known in the art (Guo et al., Endocrinology. 2010; 151(8):3502-13). Tests and assays for screening and determining whether a candidate compound is an anti-calcic drug or a compound inhibiting calcium influx into the cytoplasm may be performed by calcium quantification assay such as Fluo-4 Assay such as described in the example.

The compounds of the invention may be used or prepared in a pharmaceutical composition.

In one embodiment, the invention relates to a pharmaceutical composition comprising the compound of the invention and a pharmaceutical acceptable carrier for use in the treatment of rhabdomyolysis in a subject of need thereof.

Typically, the compound of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intra-peritoneal, intramuscular, intravenous, sub-dermal, transdermal, intrathecal and intranasal administration forms and rectal administration forms.

Preferably, the pharmaceutical compositions contain vehicles, which are pharmaceutically acceptable for a formulation capable of being injected. These may be in particular isotonic, sterile, saline solutions (monosodium or disodium phosphate, sodium, calcium or magnesium chloride and the like or mixtures of such salts), or dry, especially freeze-dried compositions which, upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compound of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chloro-butanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium mono-stearate and gelatine.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intra-peritoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time-release capsules; and any other form currently used.

Pharmaceutical compositions of the invention may include any further compound, which is used in the treatment of rhabdomyolysis. For example, the anti-rhabdomyolysis therapy may include compounds used in preventing renal function and restoring metabolic derangements such as IV fluid (IVF), isotonic saline, Lactated Ringer's, diuretics, bicarbonate, mannitol, corticosteroids, acetazolamide, antioxidants, acetaminophen, and L-carnitine; and anti-calcic drugs and compounds inhibiting calcium influx into the cytoplasm.

In one embodiment, said additional active compounds may be contained in the same composition or administrated separately.

In another embodiment, the pharmaceutical composition of the invention relates to combined preparation for simultaneous, separate or sequential use in the treatment of rhabdomyolysis in a subject in need thereof.

The invention also provides kits comprising the compound of the invention. Kits containing the compound of the invention find use in therapeutic methods.

The invention will be further illustrated by the following figures and examples. However, these examples and figures should not be interpreted in any way as limiting the scope of the present invention.

FIGURES

FIG. 1: Presence of inflammation in lipin-1 patients correlates with disease activity and is mediated by TLR9 hyper-activation.

A. B. Presence of inflammatory molecules in sera is associated with active disease. C. Inflammation is associated with hypersensitivity of patient cells (DC and macrophages) to synthetic TLR9 ligands. D. Hypersensitivity to TLR9 agonists leads to rapid maturation of DCs. E. Hypersensitivity to TLR9 agonists leads to activation of type I IFN signaling in patients. F. Inflammation is associated with hypersensitivity of patient cells (myoblasts) to synthetic TLR9 ligands. G. Pre-treatment with TLR9 antagonists or inhibitors chloroquine and primaquine is sufficient to abolish IL-6 secretion in myoblasts stimulated with CpG-A

EXAMPLES

Example 1

Material & Methods
Patients

Experiments were conducted on serum and dendritic cells (DC) and macrophages from 9 patients carrying two recessively inherited mutations in LPIN1 gene and 20 healthy age and sex-matched controls. All patients presented at least one severe rhabdomyolysis episode [21, 22]. Myoblasts from 4 age- and sex-matched controls were obtained from the cell bank of Cochin Hospital. This work has been approved by our institutional ethical committee after declaration to the Département de la Recherche Clinique et du Dévelopement and informed consent was obtained from the parents.

Muscle Biopsies and Primary Human Myoblasts

Human primary myoblasts were isolated and grown as described. CD56+ myoblasts were isolated by flow cytometry cell sorting using an anti CD56-APC conjugated antibody (e. Biosciences) and routinely maintained in F10 medium supplemented with 20% Fetal Bovine Serum (FBS).

Generation of Monocyte Derived DC

Monocytes were purified using CD14 immunomagnetic beads (Miltenyi Biotec, Paris, France) from Peripheral Blood Mononuclear Cells (PBMC) from the 9 patients and control individuals as described. Monocytes were cultured for 7 days in RPMI 1640 medium containing 10% heat inactivated FBS 100 U/mL Penicillin, and 100 µg/mL streptomycin (all from Invitrogen corporation, Paris, France), 50 ng/mL granulocyte macrophage colony-stimulating factor (GM-CSF, Miltenyi Biotec) and 100 ng/mL interleukin (IL)-4 (Miltenyi Biotec) in order to generate immature dendritic cells as described. Immature DC were harvested and transferred (106 cells/well) to 96-well plates and incubated with LipoPolySaccharide LPS (500 ng/mL), flagellin (10 ng/mL), zymosan (1 µg/mL), CpG (5 µM), imiquimod (0.5 µg/mL), poly (I: C) (1 µg/mL), or Pam3CSK4 (100 ng/mL), all from Invivogen (Toulouse, France) for 12 hours.

Cytokine Assay

After 12 hours of TLR stimulation of DC at 37° C. in humidified air containing 5% CO2, the concentrations of human IL-8, IL-6, tumor necrosis factor (TNF)-α, IL-1β, IL-10, IL-4, Monocyte Chemoattractant Protein-1 (MCP-1), RANTES (Regulated on Activation, Normal T cell Expressed and Secreted), and Macrophage Inflammatory Protein (MIP)-1-α and β in the culture supernatants were measured with a human cytokine Cytometric Bead Assay (CBA) kit (BD Biosciences, San Jose, Calif.) in accordance with the manufacturer's instructions. In brief, 50 µL of supernatant was mixed with 50 µL of mixed capture beads, and a standard curve was generated. After 3 hours of incubation at room temperature, the samples were washed and suspended in Phosphate-Buffered Saline (PBS) and then analyzed by flow cytometry (ARIA II; BD Biosciences) with CBA Analysis Software (FCAP Array version 3.0; Soft Flow, St Louis Park, Minn.). The results are expressed in picograms per milliliter.

Gene Expression Analysis

Total RNA was isolated from PBMC, DC and myoblasts using the RNeasy mini Kit and cDNA was prepared using the Quantitect Reverse Transcription Kit after depleting genomic DNA. The expression of a set of 6 interferon-stimulated genes (ISGs) in PBMC, DC and myoblasts was assessed by q-RT-PCR using Taqman Gene Expression Assays and normalized against GAPDH. Primer-Probes used were as follows IFI27—Hs01086370_m1, IFI44LHs00199115_m1, IFIT1—Hs01675197_m1, RSAD2—Hs00369813_m1, SIGLEC1—Hs00988063_m1, ISG15—Hs01921425_s1, GAPDH—Hs03929097_g1 labeled with FAM dye and amplified in a universal reaction mix. For non-type I regulated genes Primer probes used were as follows CXCL9 Hs00171065_m1, IL-12A Hs01073447_m1, and IL-6 Hs00985639_m1. Real Time quantitative PCR was performed in duplicate using the Light Cycler VIIA7 System (Roche). The RQ value is equal to 2ΔΔct where ΔΔct is calculated by (CT target—CTGAPDH) test sample—(CT target—CTGAPDH) calibrator sample. Each value is derived from three technical replicates.

Western Blotting

DC and myoblasts were lysed in 100 µl of sample buffer (2% SDS, 10% Glycerol, 0.05M Tris-HCl pH 6.8, 0.025% bromophenol blue, 0.05M DTT). Cellular protein lysates were resolved on 4%-20% SDS-PAGE gels (Biorad), transferred on nitrocellulose membrane (Biorad) and the membrane was blocked with 5% non-fat milk. Proteins were blotted with monoclonal Anti-lipin-1 (RD, AF3885), Anti-LC3 (Clone: 51-11) (MBL, M115-3) anti-p62 ( ), anti-Rab7b as primary antibody, β-Actin (AC-15) (Santa Cruz Biotechnology, sc-69879) as loading control and Alexa Fluor 680 goat anti-mouse IgG (A21057, Invitrogen) was used as secondary antibody. Membranes were scanned using Odyssey Infrared Imager (LI-COR Biosciences).

Phosphatidic Acid Phosphatase (PAP) Activity

PAP activity was measured at 37° C. for 20 min as previously described. Total PAP activity was measured in the presence of 1 mM MgCl2. PAP2 activity (Mg2+-independent) was measured in the same conditions except that MgCl2 was chelated by 2 mM EDTA. The Mg2+-dependent PAP1 activity was calculated by subtracting PAP2 activity from total enzyme activity. One unit of PAP activity was defined as the amount of enzyme that catalyzed the formation of 1 nmol of product/min. Specific activity was defined as units/mg protein.

Fluorescence Microscopy

Cell analysis by fluorescence microscopy was performed on DC and myoblasts plated on different supports including fibronectin-coated coverslips, micro-pattern slides for analysis of uniform cells. Cells were fixed, permeabilized and stained as described before. DC on day 7 were plated on fibronectin-coated 12 mm coverslips for 3 hr. in complete medium at 37° C. The cells were fixed in 4% PFA for 20 min at RT, permeabilized in 0.2% saponin/0.2% BSA in PBS, quenched in 0.2 M glycine pH 7 and incubated with antibodies. Where indicated, cells were plated on micro-pattern slides and incubated at 37° C. to allow for polarization. Images were acquired on Leica SP8 40X oil immersion objective. Images were analyzed using ImageJ and Imaris software.

Calcium Mobilization

Intracellular calcium mobilization was measured in myoblasts using the Fluo-4 Assay from Invitrogen according to the manufacturer's directions and as defined previously. Cells were loaded with 1 µm Fluo-4 for 30 min at 37° C. in 5% CO2/95% O2, as described previously (ref). The plates were then transferred to a temperature-controlled stage (Harvard Apparatus, Holliston, Mass., USA) on an Olympus IX-70 inverted microscope. Cultures were visualized using a 40×0.7 numerical aperture fluorite water-immersion objective (TC-SP8 Leica).

TLR9 Antagonists or Inhibitors

To confirm the direct participation of TLR9, myoblasts were stimulated with CpG-A (TLR9 ligand) in the presence of the G-rich inhibitory oligonucleotide (ODN-i) or after pre-treatment with chloroquine or the respective solvent control.

Vps34 Activity and PtdIns3P Production Assay

Vps34 activity was detected by visualization of PtdIns3P production on myoblasts and DC. Myoblasts and DC were respectively seeded on glass or fibronectin-coated coverslips. 24 hours later, cells were transfected with pEGFP-2xFYVE using Jet prime reagent (Polyplus). 16 hours later, the coverslips were fixed in PFA and processed for immunofluorescence to detect the GFP-2xFYVE probe, and anti-LAMP1 antibody to detect late endosome and lysosome compartments.

Autophagy Analyses

Myoblasts were stained with anti-LC3 antibody and were finally suspended in 50 µL of buffer (cold PBS with 1% FCS and 0.05% sodium azide) in 0.6 ml microcentrifuge tubes. Before running the samples, the Image Stream was calibrated using speed beads. Samples were acquired in the order of unlabeled, single color fluorescence controls (no DNA dye) and finally the experimental samples. At least 10,000-cells/experimental samples and 2000 cells/single color control were acquired for each sample. The bright field was switched of during the acquisition of single color controls. The data files were saved as .rif files (raw files). The .rif files generated from INSPIRE were analyzed using IDEAS 4.0.735 software. Single color control files were used to create compensated files (.cif) followed by generation of data (.daf) files. To obtain single cells, the doublets or clusters of cells and debris were gated out using bright field area vs. aspect ratio feature. These single cells were now gated for in focus cells based on bright field gradient root mean square (GRMS) feature (>300 GRMS). These subsets were now plotted for log intensities of channel with LC3 (autophagosome marker) and Lyso-ID or Lamp1 (lysosomal marker); they were gated for LC3+Lyso+ (double positives, in some cell populations further split into LC3highLysohigh and LC3medLysomed), LC3highLysolow (more positive for LC3), LC3lowLysohigh (more positive for lysosomal marker) and LC3lowLysolow (low for both LC3 and lysosomes) populations. Autophagy levels were calculated by measuring % colocalization in double positives of total cells by plotting these LC3hiLysohi (double positives) for bright detailed similarity (BDS) between LC3 and lysosomal markers against normalized frequency of cells. BDS on double positives mostly resulted in bimodal histograms, and gating was on the brighter peak (BDShi, mostly above 1.5 or 2). These spot masks were then converted into a feature and were used to plot against normalized frequency of cells.

ATP Measurement

ATP levels were determined with the bioluminescence assay kit HSII (Roche Applied Science, Indianapolis, Ind., USA) according to the manufacturer's instruction. Cells seeded in triplicate were washed in warm PBS. Lysates were combined with luciferase and the resulting light emission was quantified by a microplate-format luminometer. Proteins were also quantified using the Bradford kit (Sigma) and the values of luminescence were corrected to the protein level.

CTxB Uptake

Cells were washed with PBS briefly and pulsed with 1 μg/ml Alexa 594-CTxB for 30 min. After washing twice with PBS, cells were chased in the medium without CTxB for the indicated times.

siRNA

Suppressing the expression of LPIN1 gene on dendritic cells and myoblasts of donor controls was performed using siRNA specific of the gene in order to prevent further translation of the protein [31].

Lipid Droplets (LD) accumulation was visualized using bodipy staining in the skeletal myotubes as previously described [31].

Propidium Iodide (PI) and Annexin V

Propidium iodide (PI) was purchased from Sigma-Aldrich (St Louis, Mo., USA). Annexin V binding buffer and annexin V were purchased from BD Biosciences (San Jose, Calif., USA). Flow-cytometric assays were performed at our Flow Cytometry Core Facility. FluoresceinIsoThioCyanate (FITC)-conjugated Annexin V (BD Biosciences) and PI were used to detect cells undergoing apoptosis. In brief, cells were collected by centrifugation (200 g for 5 minutes at 4° C.) after experimental treatments. For staining, cells were washed twice with cold phosphate-buffered saline (PBS) and re-suspended in 1× binding buffer at a concentration 1×10$^6$ cells/ml. Then, 100 μL of solution was transferred to a 5 mL culture tube and 5 μL of annexin V-FITC and 5 μL of PI were added. Cells were gently vortexed and incubated in the dark for 15 minutes at room temperature. Prior to flow-cytometric analysis, 400 μL of 1× binding buffer was added, and cells were analyzed on a FACSCalibur™ flow cytometer (BD Biosciences, San Jose, USA) using forward-scattered light versus side-scattered light as gating parameters.

Lpin1fld/fld mice

Lpin1fld/fld mice were obtained from the Jackson Laboratory. For in vitro BM-DCs production, the bone marrow precursor cells were isolated from large bones of 6 to 16 weeks old mice. The cells were cultured for 7 days in IMDM supplemented with 10% SVF, 2 mM glutamine, 50 μM β-mercaptoethanol and J558 supernatant containing 20 μg/mL GM-CSF. The Institutional Animal Care and Use Committee of the University of Paris Descartes, Paris, approved all animal experimental protocols.

Statistical Analysis

Statistical analyses were performed using Prism 4 for Mac (Graph Pad Software). Error bars represent SEM and p values calculated with a two-tailed Mann-Whitney test unless stated otherwise.

Results

Presence of Inflammation in Lipin-1 Patients Correlates with Disease Activity and is Mediated by TLR9 Hyper-Activation.

Figure 1A:
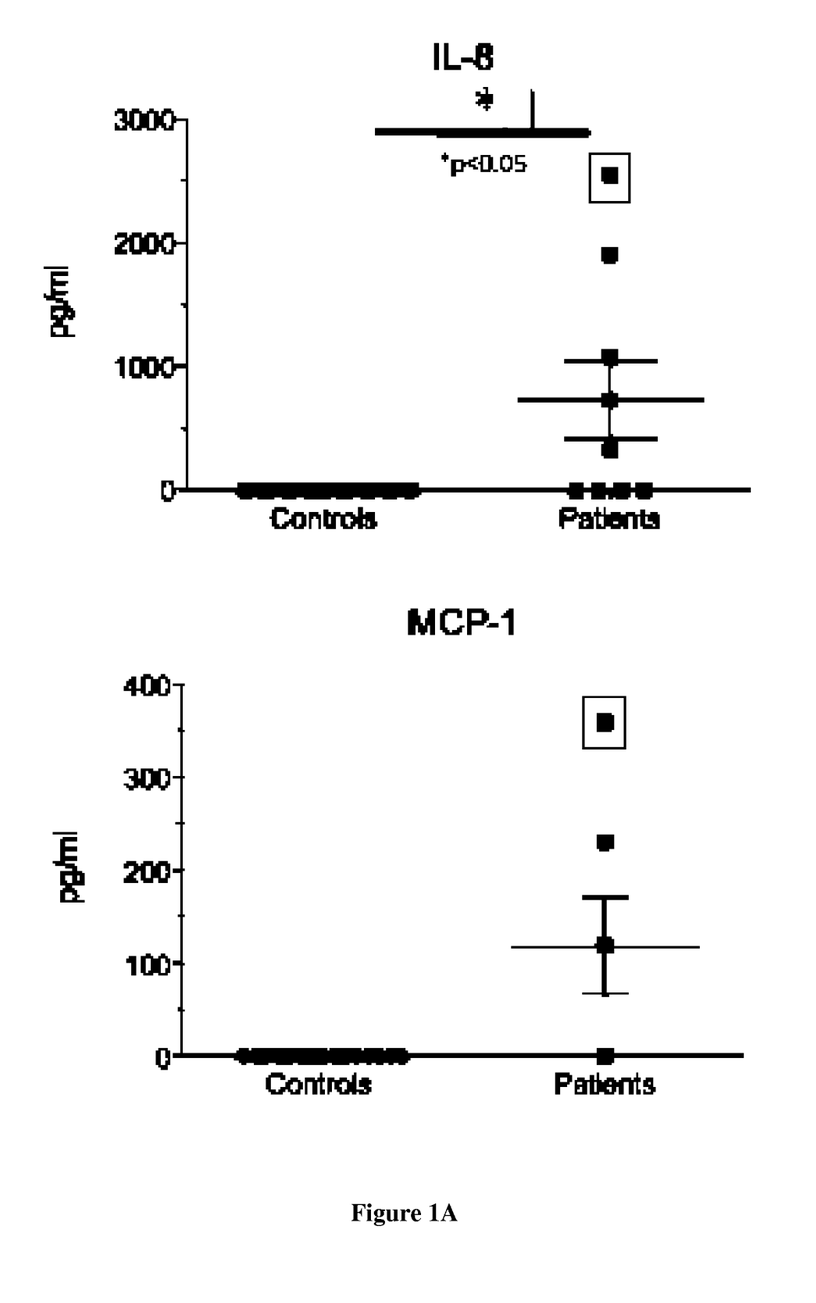
Figure 1B:
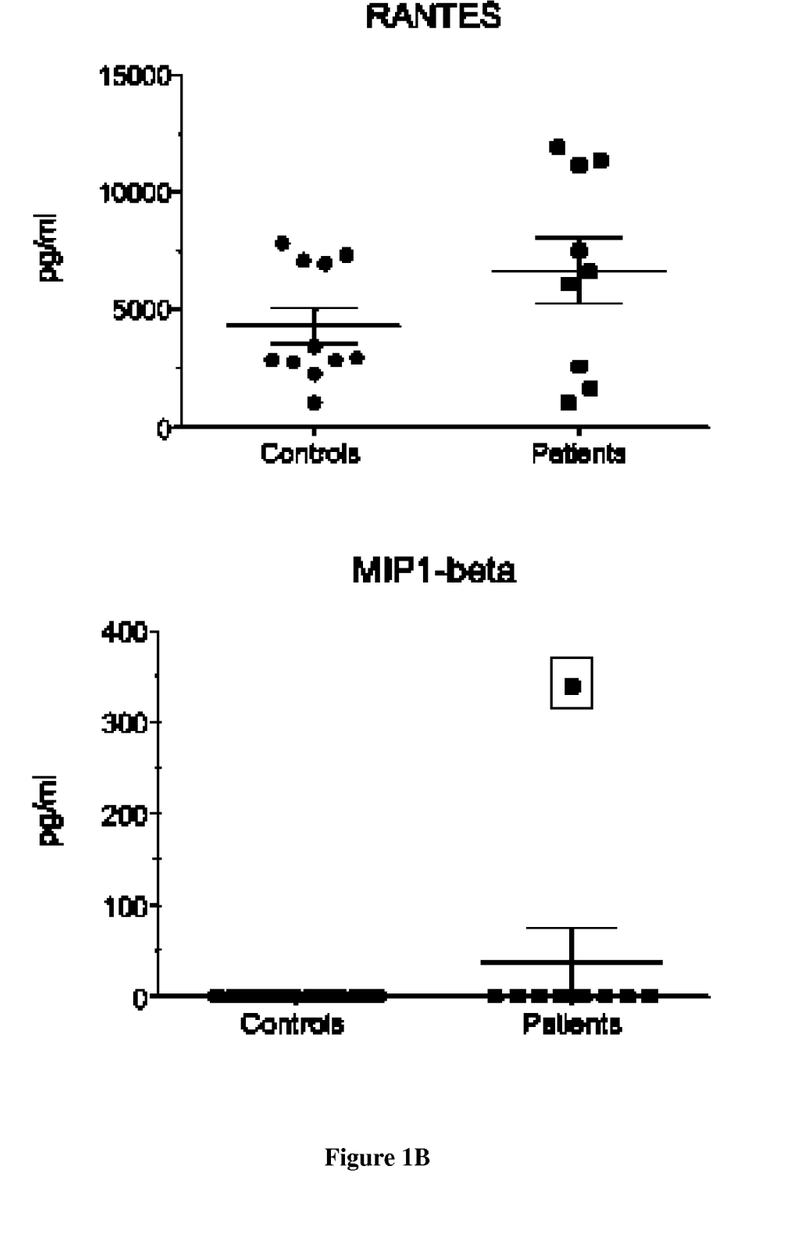
Figure 1C:
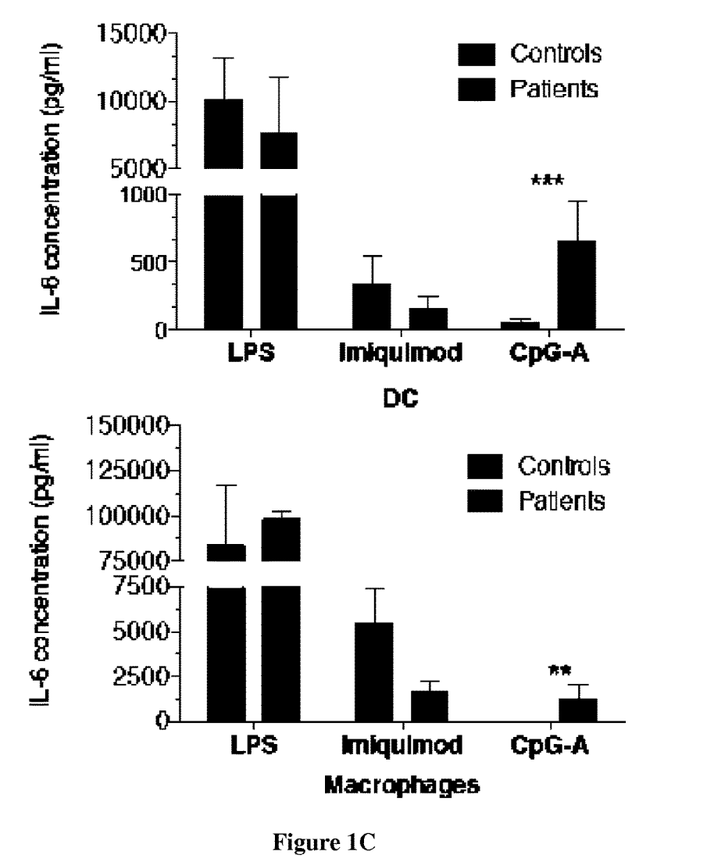
Figure 1D:
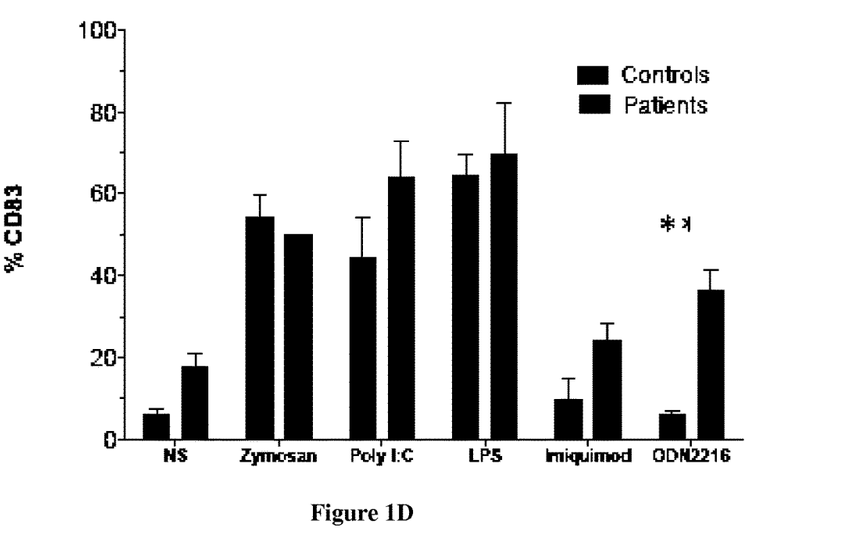
Figure 1E:
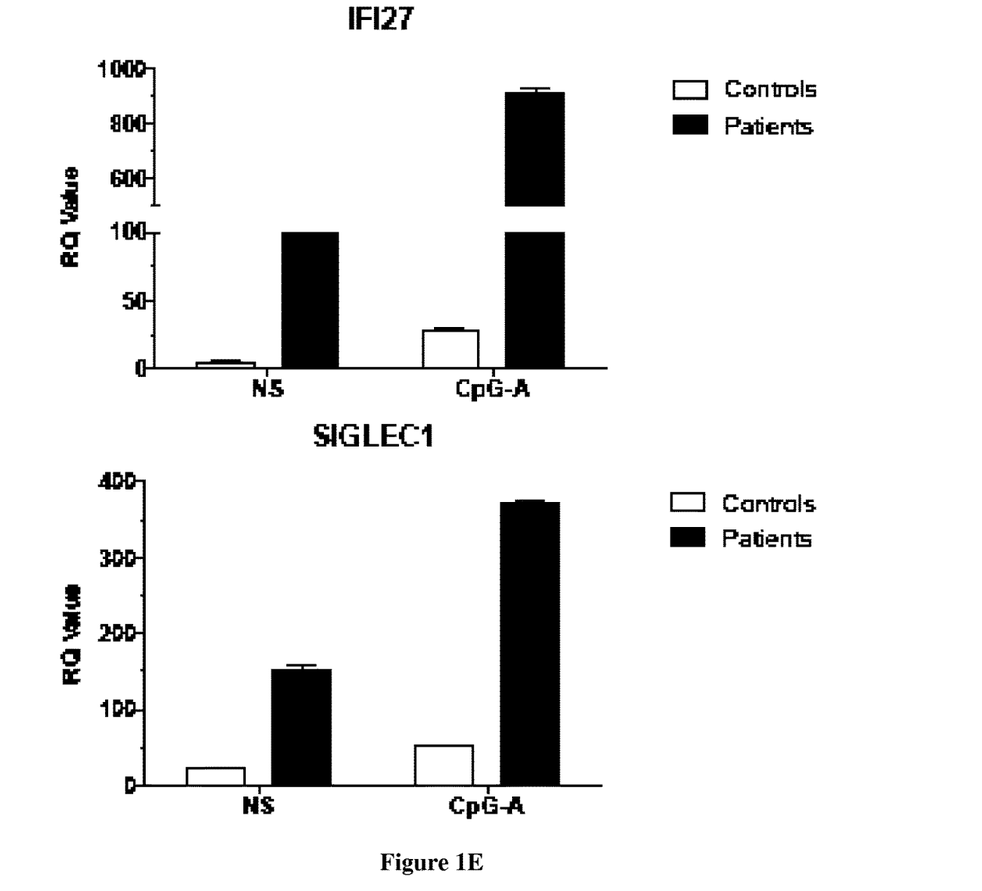
Figure 1F:
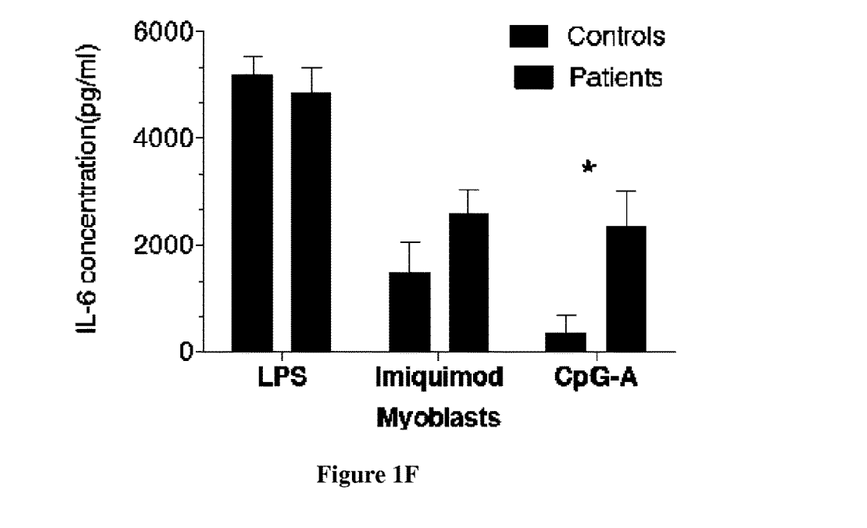
Figure 1G:
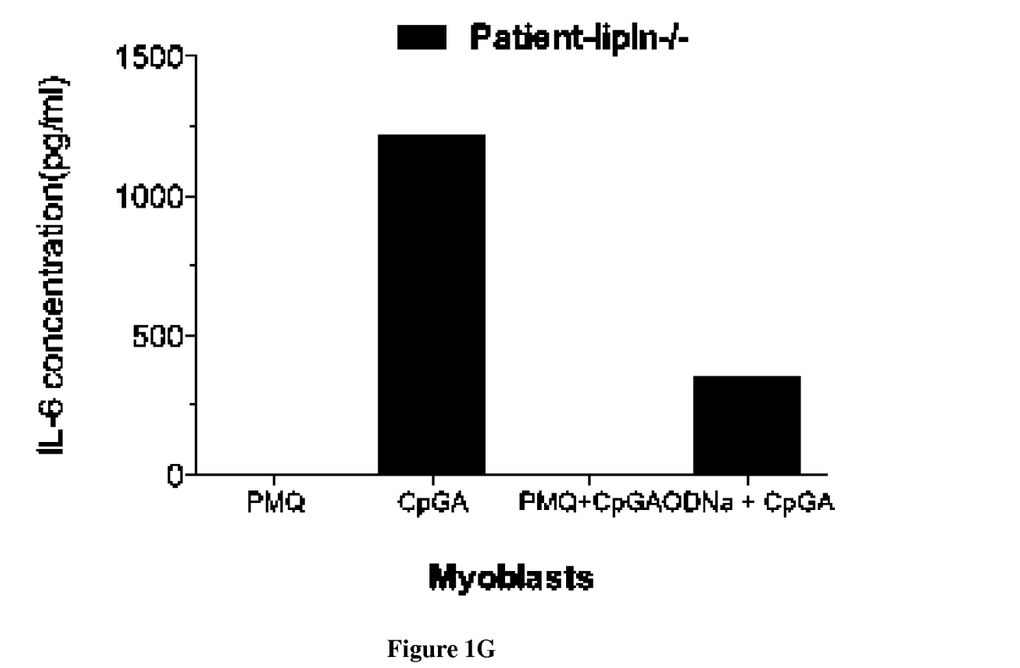

We started to collect evidence for inflammation in patients with lipin-1 mutations, by screening serum samples by a multiplex flow cytometry assay allowing for quantification of a large broad of inflammatory mediators. While most of the cytokines and chemokines tested were undetectable in sera from control individuals or patients with inactive disease, patients with a chronic evolution (n=6) or drawn during a flare (n=1) exhibited significant higher levels of RANTES, MCP-1, IL-8. More surprisingly, IFN-alpha activity was detected in patients with an active disease, an observation reminiscent of interferonopathies or viral infections (FIGS. 1A and B). We next examined the sensitivity to pathogen-associated stimuli and challenged innate immune cells from patients and control individuals with synthetic Toll-like Receptor (TLR) ligands, well-known inducers of inflammation. Surprisingly, stimulation of lipin-1 mutated DC and macrophages derived from monocytes by CpG-A only, a strong TLR9 ligand, exacerbated the secretion of inflammatory mediators (FIG. 1C). Reinforcing this unexpected result, DC derived from patients matured more rapidly after CpG-A stimulation, as reflected by the stronger surface expression of CD83 (FIG. 1D). Additionally, expression of the six Interferon Stimulated Genes (ISG) assayed (FIG. 1E), was invariably higher in patient cells compared to controls, notably for IF27 (fold increase up to 300) and to a lesser extent for SIGLEC-1 (fold increase up to 30) gene. Remarkably, in patients with chronic disease, the six ISG tested remained persistently elevated in non-stimulated cells. Because of the central role of plasmacytoid DC (pDC) in secreting IFN, we also looked for an IFN signature in these cells. As expected stimulation with CpG-A in pDC resulted in significantly increased IFN secretion in patient cells compared to controls. Hypersensitivity to TLR9 ligands extended to the major cell types expressing lipin-1 including skeletal muscle cells: myoblasts (FIG. 1F) and myotubes but not fibroblasts. Confirming the direct participation of TLR9, secretion of IL-6 after stimulation by CpG-A was abolished when myoblasts were pre-treated with G-rich inhibitory oligonucleotide (ODN-i). We have also shown that the pre-treatment with chloroquine and primaquine is sufficient to attenuate or abolish IL-6 secretion in myoblasts stimulated with CpG-A (FIG. 1G). Finally we could recapitulate hypersensitivity of patient cells to natural TLR9 ligands after exposing myoblasts to UVA-inactivated HSV-1 (Sato et al, 2006). Following infection, significant elevation of the inflammatory cytokine IL-6 was seen in myoblasts from patients compared to controls. To obtain direct evidence for a causative role of lipin-1, we investigated whether lipin-1 deficiency was involved in TLR9 ligand hypersensitivity by transfecting a plasmid coding for lipin-1-GFP in myoblasts from patients. Transfected cells stimulated with CpG-A secreted similar level of IL-6 compared to controls. In contrast, when bone marrow derived DC from Lpin1fld/fld mice or from lipin-1 Knock Out rats were challenged with CpG-A comparable level of IL-6 were observed in both DC from wild type and K.O animals for lipin-1. This result suggested that hypersensitivity to TLR9 ligands was restricted to human lipin-1 deficiency and not reproduced in rodent models.

Defective PAP1 Activity in Patients' Innate Immune Cells is Responsible for an Accelerated TLR9 Trafficking to Lysosomes and Signalling.

Figure 2:
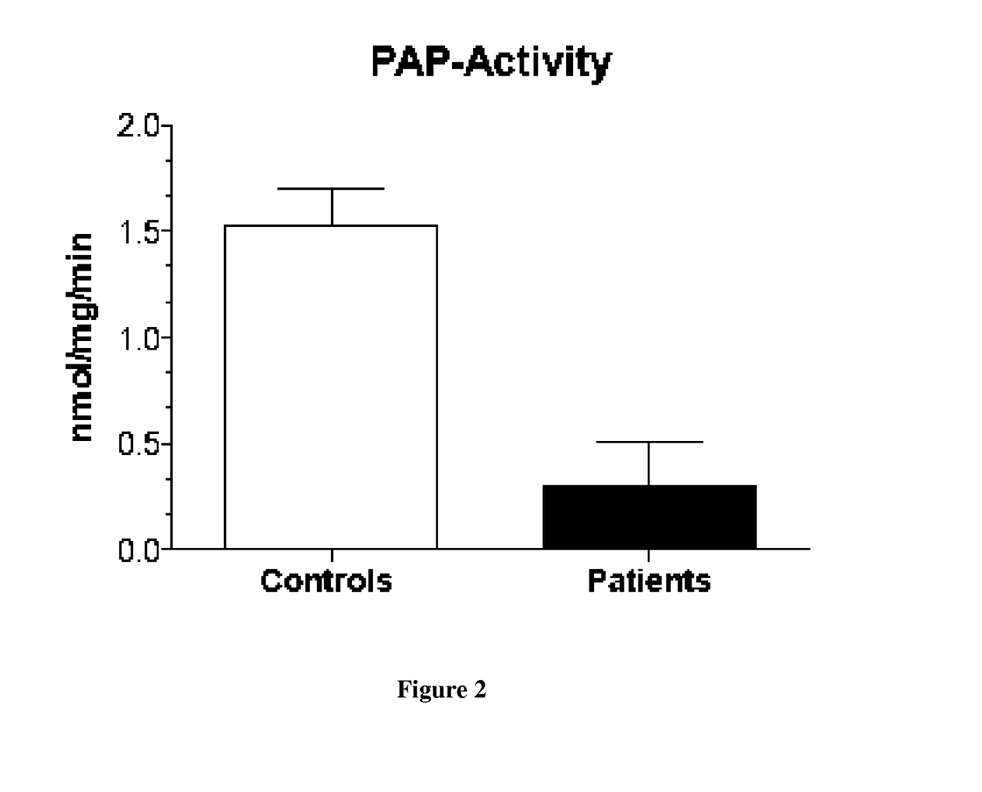
FIG. 2: Defective PAP1 activity in patients' DC.

To obtain insight in the aberrant activation of TLR9 in patients' cells, we analysed IRF-7 and NF-kb signaling pathways during time course stimulation with CpG-A or irrelevant TLR-agonists. We observed earlier recruitment and activation of molecules specifically recruited to this pathway. Because TLR9 gene and protein expression were similar between patients and controls, our attention focused on TLR9 trafficking to late endosomes and lysosomes, a physiological process well known to be tightly regulated and related to its activation. A time course tracking of fluorescent CpG-A or TLR9 by confocal microscopy revealed that in the absence of any stimulation both were significantly co-localizing with Lamp-1 only in patients' cells, this difference being more prominent with time: T0, 10% vs. 40% p<0.0001; T20, 45% vs. 65%, p<0.0001. To clarify the direct contribution of lipin-1 in our observation, we investigated the consequences of mutations in expression and functions. Importantly lipin-1 was expressed in DCs and macrophages as evaluated by Western blots and mutations induced either an unstable protein or a C-terminus-truncated protein. Confocal imaging confirmed that lipin-1 expression was maintained but its subcellular distribution drastically varied from wild-type condition, especially with a more scarce nuclear localization compared to control cells. As expected due to mutations residual PAP1-specific activity was almost undetectable in patient cells (FIG. 2). Importantly, over-expression of wild type lipin-1 in patient cells corrected hypersensitivity to TLR9 agonists whereas over-expression of mutant proteins induced it, providing direct evidence for a causal role for lipin-1 mutations in the cell biological perturbation observed.

TLR9 Ligands Hyper-Sensibility Contributes to Muscle Damage in Patients.

To evaluate the link between muscle damage and inflammation, we explored TLR ligand involvement in the control of intracellular Ca2+ dynamics, as its intracellular increase is the hallmark of rhabdomyolysis. The levels of intracellular Ca2+ recorded using live imaging of resting cells were equivalent among control and patient cells. As expected treatment with ionomycin induced a rapid calcium flux in control and patient myoblasts, while stimulation with CpG-A induced an immediate increase of the intracellular calcium concentration only in patient cells. This effect observed with patient cells was specific for TLR9 ligands since no response was observed following exposure to LPS or Imiquimod in both patient and control cells. Pre-treatment with 10 µM of chloroquine or ODN-i abolished intracellular calcium mobilization in patient cells in presence of CpG-A completely. Chelation of intracellular calcium using dantrium also inhibited elevation of intracellular calcium. These data indicated that an aberrant activation of TLR9 is responsible for an increase of intracellular calcium flux in patient cells and potentially for rhabdomyolysis. To obtain additional evidence for the role of inflammation in muscle damage, we measured ATP production in myoblasts following stimulation with CpG-A; we found an impairment of ATP production following stimulation with inflammatory stimuli in patient cells compared to control. To confirm the deleterious effect of TLR9 ligands in patient myoblasts, we incubated myoblasts with increasing doses of CpG-A and measured cellular mortality at different time point as accessed by the viability assay. Myoblasts from patients were exclusively sensitive to TLR9 ligands.

Next, we asked if autophagy contributed independently to, or potentiated the effect of, TLR9 ligands in triggering rhabdomyolysis, since it has been published a direct role of a defect of autophagy clearance in rhabdomyolysis statin-induced in mice. We accessed the induction of autophagy by examining the levels of the autophagosome marker, microtubule-associated protein-1 light Chain 3 (LC3)-II. In control myoblasts, the induction of autophagy by serum and amino acid starvation led to the expected induction of LC3-II, which was not apparent after feeding. Myoblasts from patients induced autophagosome formation in response to fasting but maintained high levels of LC3-II even after refeeding. Interestingly treatment with rapamycin, which inhibits mTOR and induces autophagy, induced a modest increase in LC3-II level in controls albeit less than that observed in lipin-1 deficient myoblasts under basal conditions. We also estimated autophagic flux by quantitating the levels of p62, an autophagy selective substrate. Compared to controls, lipin-1 deficient myoblasts accumulated twice as much p62. These results suggest that lipin-1 is dispensable for the formation of autophagosomes but is required for clearance of autolysosome cargo. We next accessed whether the hyper-sensibility to TLR9 ligation observed in lipin-1 deficient myoblasts exacerbated the defect in autophagosome clearance. However, treatment of myoblasts from patients with CpG-A did not affect either autophagosome formation or the clearance of autophagosomes.

To learn more about the role of lipin-1 deficiency in autophagosome clearance, we examined the global autolysosome architecture in the absence of lipin-1.

The Global Endosomal Architecture is Altered in Cells from Patients with Lipin-1 Mutations.

We wondered how the absence of lipin-1 affected TLR-9 trafficking in lipin-1 related disease. To address this, we analyzed the global integrity of cellular compartments in DCs from patients by confocal microscopy. As expected staining of control DC with specific antibodies for Rab14 and EEA1 (Early Endosome Antigen 1) confirmed colocalization of the two markers in the cellular periphery, which was also found for Syntaxin6 and EEA-1. However in patient cells, these vesicles accumulated in a central compartment, probably corresponding to the Trans-Golgi Network (TGN), rather than in the periphery. Additionally, in some patient cells, Rab14 positive vesicles could be observed in the periphery where they showed significant and highly unusual co-localization with Lysosomal Associated Markers (LAMP)-1 and LAMP-2. The tight regulation of TLR9 signalling is governed by several actors: for instance the small GTPase (Ras related in brain) Rab7b which shares a very high homology with Rab7 has been recently identified as a negative regulator of TLR9 signaling in immune cells by enhancing its trafficking to late endosomes/lysosomes and its degradation.

Loss of PAP-1 Activity Leads to Defective PI3K Activity and Rab7b Mis-Localization.

A decrease of PI3K was found in patient DCs compared to control cells with a consecutive decrease of Rab7b in patient DCs (right) compared to control.

Loss of PAP-1 Activity Leads to Defective Retrograde Transport.

It has been previously shown, that Rab7b is involved in controlling retrograde transport protein through late endosomes to the Trans Golgi Network. We first examined the effect of a mis-localization of Rab7b in lipin-1 deficiency on CTxB transport. In control cells, CTxB accumulated in TGN after a 15-min chase, and showed a good co-localization with GM130 after a 30-min chase, confirming the CTxB transport from the PM through the TGN. In cells depleted of SMAP2 with siRNA #1, the transport of CTxB from REs to the Golgi, not from the PM to REs, was significantly impaired. After a 60-min chase, CTxB still accumulated in REs, and did not co-localize with GM130. By counting the number of cells in which CTxB did not reach the Golgi, more than 80% of the cells depleted of SMAP2 with siRNA #1 displayed the defect of the CTxB transport from REs to the Golgi. The other two siRNAs #2 and #3 also impaired the CTxB transport.

Example 2

Figure 3:
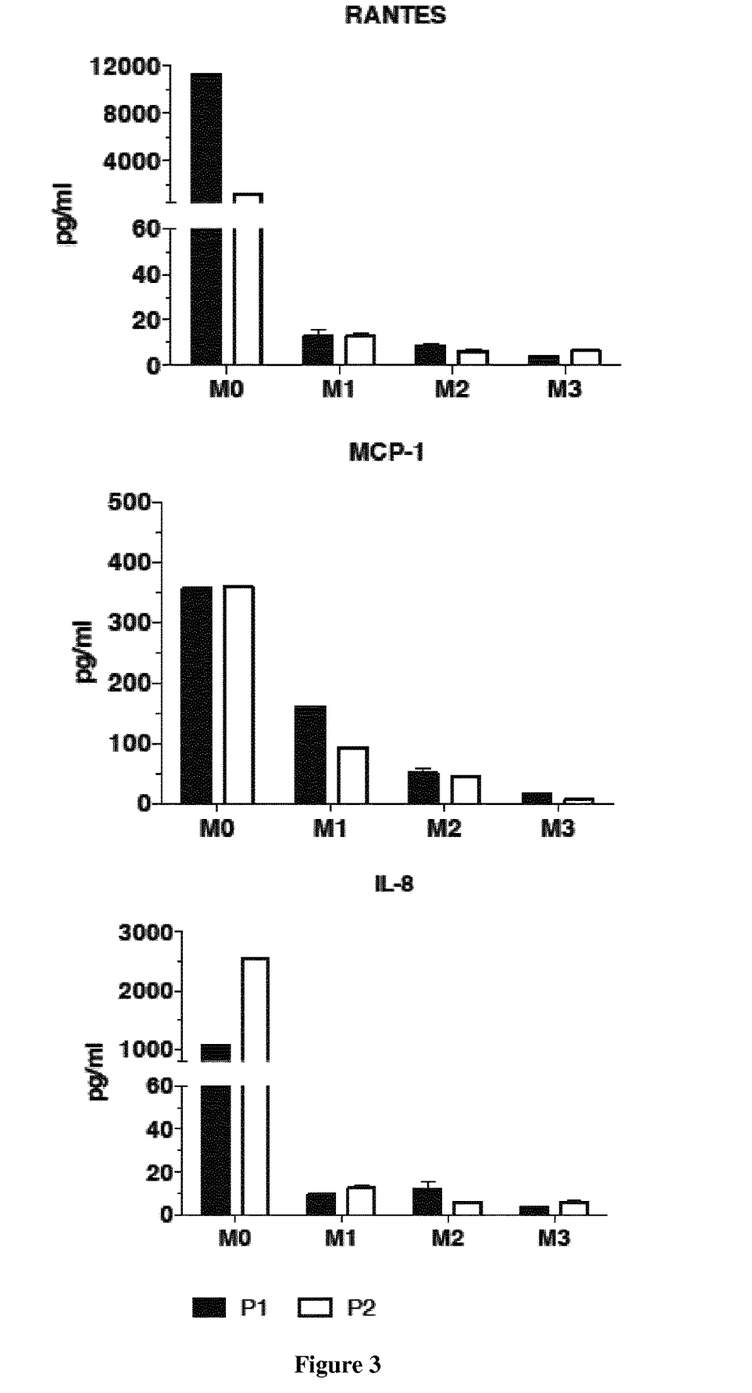
FIG. 3: Treatment with hydroxychloroquine (Plaquenil®, 6 mg/Kg/day) induces a dramatic decrease of pro-inflammatory cytokines (IL-8, RANTES, MCP-1) in patient's sera.

Two patients were treated with hydroxychloroquine (Plaquenil®, 6 mg/Kg/day). At three months of treatments, the inventors observed a decrease of muscle pain and a dramatic decrease of pro-inflammatory cytokines (IL-8, RANTES, MCP-1) in sera (FIG. 3).

REFERENCES

Throughout this application, various references describe the state of the art to which this invention pertains. The disclosures of these references are hereby incorporated by reference into the present disclosure.

[1] J. M. Sauret, G. Marinides, G. K. Wang, Rhabdomyolysis, American family physician, 65 (2002) 907-912.
[2] G. Cervellin, I. Comelli, G. Lippi, Rhabdomyolysis: historical background, clinical, diagnostic and therapeutic features, Clinical chemistry and laboratory medicine: CCLM/FESCC, 48 (2010) 749-756.
[3] R. P. Luck, S. Verbin, Rhabdomyolysis: a review of clinical presentation, etiology, diagnosis, and management, Pediatric emergency care, 24 (2008) 262-268.
[4] M. L. Shapiro, A. Baldea, F. A. Luchette, Rhabdomyolysis in the intensive care unit, Journal of intensive care medicine, 27 (2012) 335-342.
[5] M. H. Zhang, Rhabdomyolosis and its pathogenesis, World journal of emergency medicine, 3 (2012) 11-15.
[6] G. S. Hotamisligil, N. S. Shargill, B. M. Spiegelman, Adipose expression of tumor necrosis factor-alpha: direct role in obesity-linked insulin resistance, Science, 259 (1993) 87-91.
[7] H. Xu, G. T. Barnes, Q. Yang, G. Tan, D. Yang, C. J. Chou, J. Sole, A. Nichols, J. S. Ross, L. A. Tartaglia, H. Chen, Chronic inflammation in fat plays a crucial role in the development of obesity-related insulin resistance, The Journal of clinical investigation, 112 (2003) 1821-1830.
[8] S. P. Weisberg, D. McCann, M. Desai, M. Rosenbaum, R. L. Leibel, A. W. Ferrante, Jr., Obesity is associated with macrophage accumulation in adipose tissue, The Journal of clinical investigation, 112 (2003) 1796-1808.
[9] A. Mamoune, M. Bahuau, Y. Hamel, V. Serre, M. Pelosi, F. Habarou, M. A. Nguyen Morel, B. Boisson, S. Vergnaud, M. T. Viou, L. Nonnenmacher, M. Piraud, P. Nusbaum, J. Vamecq, N. Romero, C. Ottolenghi, J. L. Casanova, P. de Lonlay, A Thermolabile Aldolase A Mutant Causes Fever-Induced Recurrent Rhabdomyolysis without Hemolytic Anemia, PLoS genetics, 10 (2014) e1004711.
[10] D. Mathis, S. E. Shoelson, Immunometabolism: an emerging frontier, Nature reviews. Immunology, 11 (2011) 81.
[11] T. Herlin, B. Fiirgaard, M. Bjerre, G. Kerndrup, H. Hasle, X. Bing, P. J. Ferguson, Efficacy of anti-IL-1 treatment in Majeed syndrome, Annals of the rheumatic diseases, (2012).
[12] H. A. Majeed, M. Al-Tarawna, H. El-Shanti, B. Kamel, F. Al-Khalaileh, The syndrome of chronic recurrent multifocal osteomyelitis and congenital dyserythropoietic anaemia. Report of a new family and a review, European journal of pediatrics, 160 (2001) 705-710.
[13] L. M. Kuijk, J. M. Beekman, J. Koster, H. R. Waterham, J. Frenkel, P. J. Coffer, HMG-CoA reductase inhibition induces IL-1beta release through Rac1/PI3K/PKB-dependent caspase-1 activation, Blood, 112 (2008) 3563-3573.
[14] M. Valdearcos, E. Esquinas, C. Meana, L. Pena, L. Gil-de-Gomez, J. Balsinde, M. A. Balboa, Lipin-2 reduces proinflammatory signaling induced by saturated Fatty acids in macrophages, The Journal of biological chemistry, 287 (2012) 10894-10904.
[15] P. J. Ferguson, M. Sandu, Current understanding of the pathogenesis and management of chronic recurrent multifocal osteomyelitis, Current rheumatology reports, 14 (2012) 130-141.
[16] S. W. Sauer, J. G. Okun, M. A. Schwab, L. R. Crnic, G. F. Hoffmann, S. I. Goodman, D. M. Koeller, S. Kolker, Bioenergetics in glutaryl-coenzyme A dehydrogenase deficiency: a role for glutaryl-coenzyme A, The Journal of biological chemistry, 280 (2005) 21830-21836.
[17] S. Kolker, D. M. Koeller, J. G. Okun, G. F. Hoffmann, Pathomechanisms of neurodegeneration in glutaryl-CoA dehydrogenase deficiency, Annals of neurology, 55 (2004) 7-12.
[18] C. C. Chao, S. Hu, Tumor necrosis factor-alpha potentiates glutamate neurotoxicity in human fetal brain cell cultures, Developmental neuroscience, 16 (1994) 172-179.
[19] J. Lamp, B. Keyser, D. M. Koeller, K. Ullrich, T. Braulke, C. Muhlhausen, Glutaric aciduria type 1 metabolites impair the succinate transport from astrocytic to neuronal cells, The Journal of biological chemistry, 286 (2011) 17777-17784.
[20] A. Zeharia, A. Shaag, R. H. Houtkooper, T. Hindi, P. de Lonlay, G. Erez, L. Hubert, A. Saada, Y. de Keyzer, G. Eshel, F. M. Vaz, O. Pines, O. Elpeleg, Mutations in LPIN1 cause recurrent acute myoglobinuria in childhood, American journal of human genetics, 83 (2008) 489-494.
[21] C. Michot, L. Hubert, M. Brivet, L. De Meirleir, V. Valayannopoulos, W. Muller-Felber, R. Venkateswaran, H. Ogier, I. Desguerre, C. Altuzarra, E. Thompson, M. Smitka, A. Huebner, M. Husson, R. Horvath, P. Chinnery, F. M. Vaz, A. Munnich, O. Elpeleg, A. Delahodde, Y. de Keyzer, P. de Lonlay, LPIN1 gene mutations: a major cause of severe rhabdomyolysis in early childhood, Human mutation, 31 (2010) E1564-1573.

[22] C. Michot, L. Hubert, N. B. Romero, A. Gouda, A. Mamoune, S. Mathew, E. Kirk, L. Viollet, S. Rahman, S. Bekri, H. Peters, J. McGill, E. Glamuzina, M. Farrar, M. von der Hagen, I. E. Alexander, B. Kirmse, M. Barth, P. Laforet, P. Benlian, A. Munnich, M. Jeanpierre, O. Elpeleg, O. Pines, A. Delahodde, Y. de Keyzer, P. de Lonlay, Study of LPIN1, LPIN2 and LPIN3 in rhabdomyolysis and exercise-induced myalgia, Journal of inherited metabolic disease, (2012).

[23] J. Bergounioux, A. Brassier, C. Rambaud, O. Bustarret, C. Michot, L. Hubert, J. B. Arnoux, A. Laquerriere, S. Bekri, S. Galene-Gromez, D. Bonnet, P. Hubert, P. de Lonlay, Fatal rhabdomyolysis in 2 children with LPIN1 mutations, The Journal of pediatrics, 160 (2012) 1052-1054.

[24] G. G. Schweitzer, S. L. Collier, Z. Chen, J. M. Eaton, A. M. Connolly, R. C. Bucelli, A. Pestronk, T. E. Harris, B. N. Finck, Rhabdomyolysis-Associated Mutations in Human LPIN1 Lead to Loss of Phosphatidic Acid Phosphohydrolase Activity, JIMD reports, (2015).

[25] J. Donkor, M. Sariahmetoglu, J. Dewald, D. N. Brindley, K. Reue, Three mammalian lipins act as phosphatidate phosphatases with distinct tissue expression patterns, The Journal of biological chemistry, 282 (2007) 3450-3457.

[26] G. S. Han, W. I. Wu, G. M. Carman, The Saccharomyces cerevisiae Lipin homolog is a Mg2+-dependent phosphatidate phosphatase enzyme, The Journal of biological chemistry, 281 (2006) 9210-9218.

[27] B. N. Finck, M. C. Gropler, Z. Chen, T. C. Leone, M. A. Croce, T. E. Harris, J. C. Lawrence, Jr., D. P. Kelly, Lipin 1 is an inducible amplifier of the hepatic PGC-1alpha/PPARalpha regulatory pathway, Cell metabolism, 4 (2006) 199-210.

[28] H. B. Kim, A. Kumar, L. Wang, G. H. Liu, S. R. Keller, J. C. Lawrence, Jr., B. N. Finck, T. E. Harris, Lipin 1 represses NFATc4 transcriptional activity in adipocytes to inhibit secretion of inflammatory factors, Molecular and cellular biology, 30 (2010) 3126-3139.

[29] T. R. Peterson, S. S. Sengupta, T. E. Harris, A. E. Carmack, S. A. Kang, E. Balderas, D. A. Guertin, K. L. Madden, A. E. Carpenter, B. N. Finck, D. M. Sabatini, mTOR complex 1 regulates lipin 1 localization to control the SREBP pathway, Cell, 146 (2011) 408-420.

[30] M. C. Sugden, P. W. Caton, M. J. Holness, PPAR control: it's SIRTainly as easy as PGC, The Journal of endocrinology, 204 (2010) 93-104.

[31] C. Michot, A. Mamoune, J. Vamecq, M. T. Viou, L. S. Hsieh, E. Testet, J. Laine, L. Hubert, A. F. Dessein, M. Fontaine, C. Ottolenghi, L. Fouillen, K. Nadra, E. Blanc, J. Bastin, S. Candon, M. Pende, A. Munnich, A. Smahi, F. Djouadi, G. M. Carman, N. Romero, Y. de Keyzer, P. de Lonlay, Combination of lipid metabolism alterations and their sensitivity to inflammatory cytokines in human lipin-1-deficient myoblasts, Biochimica et biophysica acta, 1832 (2013) 2103-2114.

[32] P. Zhang, M. A. Verity, K. Reue, Lipin-1 Regulates Autophagy Clearance and Intersects with Statin Drug Effects in Skeletal Muscle, Cell metabolism, (2014).

[33] M. Valdearcos, E. Esquinas, C. Meana, L. Gil-de-Gomez, C. Guijas, J. Balsinde, M. A. Balboa, Subcellular localization and role of lipin-1 in human macrophages, Journal of immunology, 186 (2011) 6004-6013.

[34] A. R. Navratil, A. M. Brummett, J. D. Bryan, M. D. Woolard, Francisella tularensis LVS induction of prostaglandin biosynthesis by infected macrophages requires specific host phospholipases and lipid phosphatases, Infection and immunity, (2014).

[35] C. Meana, L. Pena, G. Lorden, E. Esquinas, C. Guijas, M. Valdearcos, J. Balsinde, M. A. Balboa, Lipin-1 Integrates Lipid Synthesis with Proinflammatory Responses during TLR Activation in Macrophages, Journal of immunology, 193 (2014) 4614-4622.

[36] H. Kanda, S. Tateya, Y. Tamori, K. Kotani, K. Hiasa, R. Kitazawa, S. Kitazawa, H. Miyachi, S. Maeda, K. Egashira, M. Kasuga, MCP-1 contributes to macrophage infiltration into adipose tissue, insulin resistance, and hepatic steatosis in obesity, The Journal of clinical investigation, 116 (2006) 1494-1505.

[37] C. A. Janeway, Jr., R. Medzhitov, Innate immune recognition, Annual review of immunology, 20 (2002) 197-216.

[38] E. L. Pearce, E. J. Pearce, Metabolic pathways in immune cell activation and quiescence, Immunity, 38 (2013) 633-643.

[39] G. R. Robbins, H. Wen, J. P. Ting, Inflammasomes and metabolic disorders: old genes in modern diseases, Molecular cell, 54 (2014) 297-308.

[40] R. Barbalat, S. E. Ewald, M. L. Mouchess, G. M. Barton, Nucleic acid recognition by the innate immune system, Annual review of immunology, 29 (2011) 185-214.

[41] M. de Bernard, R. Rizzuto, Toll-like receptors hit calcium, EMBO reports, 15 (2014) 468-469.

[42] R. Jahn, T. C. Sudhof, Membrane fusion and exocytosis, Annual review of biochemistry, 68 (1999) 863-911.

[43] C. Bucci, O. Bakke, C. Progida, Rab7b and receptors trafficking, Communicative & integrative biology, 3 (2010) 401-404.

[44] M. Yang, T. Chen, C. Han, N. Li, T. Wan, X. Cao, Rab7b, a novel lysosome-associated small GTPase, is involved in monocytic differentiation of human acute promyelocytic leukemia cells, Biochemical and biophysical research communications, 318 (2004) 792-799.

[45] C. Progida, L. Cogli, F. Piro, A. De Luca, O. Bakke, C. Bucci, Rab7b controls trafficking from endosomes to the TGN, Journal of cell science, 123 (2010) 1480-1491.

[46] M. Borg, O. Bakke, C. Progida, A novel interaction between Rab7b and actomyosin reveals a dual role in intracellular transport and cell migration, Journal of cell science, (2014).

[47] J. E. Vance, Phospholipid Synthesis and Transport in Mammalian Cells, Traffic, (2014).

[48] F. Kano, T. Arai, M. Matsuto, H. Hayashi, M. Sato, M. Murata, Hydrogen peroxide depletes phosphatidylinositol-3-phosphate from endosomes in a p38 MAPK-dependent manner and perturbs endocytosis, Biochimica et biophysica acta, 1813 (2011) 784-801.

[49] K. O. Schink, C. Raiborg, H. Stenmark, Phosphatidylinositol 3-phosphate, a lipid that regulates membrane dynamics, protein sorting and cell signalling, BioEssays: news and reviews in molecular, cellular and developmental biology, 35 (2013) 900-912.

[50] R. Zoncu, R. M. Perera, D. M. Balkin, M. Pirruccello, D. Toomre, P. De Camilli, A phosphoinositide switch controls the maturation and signaling properties of APPL endosomes, Cell, 136 (2009) 1110-1121.

[51] C. Raiborg, K. O. Bache, A. Mehlum, H. Stenmark, Function of Hrs in endocytic trafficking and signalling, Biochemical Society transactions, 29 (2001) 472-475.

[52] N. Fili, V. Calleja, R. Woscholski, P. J. Parker, B. Larijani, Compartmental signal modulation: Endosomal phosphatidylinositol 3-phosphate controls endosome morphology and selective cargo sorting, Proceedings of the National Academy of Sciences of the United States of America, 103 (2006) 15473-15478.

[53] D. Poccia, B. Larijani, Phosphatidylinositol metabolism and membrane fusion, The Biochemical journal, 418 (2009) 233-246.

[54] D. J. Gillooly, I. C. Morrow, M. Lindsay, R. Gould, N. J. Bryant, J. M. Gaullier, R. G. Parton, H. Stenmark, Localization of phosphatidylinositol 3-phosphate in yeast and mammalian cells, The EMBO journal, 19 (2000) 4577-4588.

[55] A. Jeschke, N. Zehethofer, B. Lindner, J. Krupp, D. Schwudke, I. Haneburger, M. Jovic, J. M. Backer, T. Balla, H. Hilbi, A. Haas, Phosphatidylinositol 4-phosphate and phosphatidylinositol 3-phosphate regulate phagolysosome biogenesis, Proceedings of the National Academy of Sciences of the United States of America, 112 (2015) 4636-4641.

[56] I. Ribeiro, L. Yuan, G. Tanentzapf, J. J. Dowling, A. Kiger, Phosphoinositide regulation of integrin trafficking required for muscle attachment and maintenance, PLoS genetics, 7 (2011) e1001295.

[57] T. Sasser, Q. S. Qiu, S. Karunakaran, M. Padolina, A. Reyes, B. Flood, S. Smith, C. Gonzales, R. A. Fratti, Yeast lipin 1 orthologue pahlp regulates vacuole homeostasis and membrane fusion, The Journal of biological chemistry, 287 (2012) 2221-2236.

The invention claimed is:

1. A method for treating rhabdomyolysis in a subject in need thereof, comprising the step of administering to said subject a at least one compound selected from the group consisting of one or more TLR9 antagonists and one or more inhibitors of TLR9 expression.

2. The method according to claim 1, wherein said one or more TLR9 antagonists is a small organic molecule, an oligonucleotide, a polypeptide, an aptamer, or an intra-antibody.

3. The method according to claim 2, wherein said small organic molecule is selected from the group consisting of chloroquine, primaquine, imidazoquinolines, 4-Amino-quinolines, quinazolines, CMZ 203-84, CMZ 203-85, CMZ 203-88, CMZ 203-88-1, CMZ 203-89, CMZ 203-91, hydroxychloroquine, quinacrine, bafilomycin A, and CPG52364.

4. The method according to claim 2, wherein said oligonucleotide is CpG ODNi.

5. The method according to claim 1, wherein the one or more TLR9 antagonists and the one or more inhibitors of TLR9 expression are administered in combination with one or more anti-rhabdomyolysis compounds.

6. The method according to claim 5 wherein said one or more anti-rhabdomyolysis compounds is a compound inhibiting calcium influx.

7. The method of claim 6, wherein the compound inhibiting calcium influx is dantrium.

\* \* \* \* \*